United States Patent
Xu et al.

(10) Patent No.: US 11,571,374 B2
(45) Date of Patent: Feb. 7, 2023

(54) ORAL CARE PRODUCT AND METHODS OF USE AND MANUFACTURE THEREOF

(71) Applicant: Colgate-Palmolive Company, New York, NY (US)

(72) Inventors: Yun Xu, Langhorne, PA (US); Stacey Lavender, Chesterfield, NJ (US); Luciana Rinaudi Marron, Somerset, NJ (US); Zoe Scoullos, South River, NJ (US); Manish Mandhare, Navi Mumbai (IN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/829,012

(22) Filed: Mar. 25, 2020

(65) Prior Publication Data
US 2020/0306159 A1 Oct. 1, 2020

Related U.S. Application Data

(60) Provisional application No. 62/825,952, filed on Mar. 29, 2019.

(51) Int. Cl.
*A61K 8/44* (2006.01)
*A61K 8/24* (2006.01)
*A61Q 11/00* (2006.01)

(52) U.S. Cl.
CPC .................. *A61K 8/44* (2013.01); *A61K 8/24* (2013.01); *A61Q 11/00* (2013.01)

(58) Field of Classification Search
CPC ....................................................... A61Q 11/00
See application file for complete search history.

(56) References Cited

U.S. PATENT DOCUMENTS

| | | | |
|---|---|---|---|
| 9,682,026 B2 | 6/2017 | Kohli et al. | |
| 9,682,027 B2 | 6/2017 | Prencipe et al. | |
| 9,717,929 B2 | 8/2017 | Chopra et al. | |
| 10,226,410 B2 | 3/2019 | Yang et al. | |
| 11,020,329 B2 * | 6/2021 | Potnis | A61K 8/44 |
| 2009/0202450 A1 * | 8/2009 | Prencipe | A61K 8/19 424/50 |
| 2009/0202456 A1 | 8/2009 | Prencipe et al. | |
| 2010/0135932 A1 * | 6/2010 | Deckner | A61Q 11/00 424/52 |
| 2013/0263395 A1 * | 10/2013 | Boyd | A61K 8/11 15/104.94 |
| 2014/0227202 A1 * | 8/2014 | Pilgaonkar | A61Q 11/00 424/53 |
| 2015/0086493 A1 * | 3/2015 | Guery | A61K 8/26 424/57 |
| 2015/0305993 A1 * | 10/2015 | Rege | A61K 8/44 424/54 |
| 2018/0296453 A1 | 10/2018 | Prencipe et al. | |

FOREIGN PATENT DOCUMENTS

WO    WO-2017219339 A1 * 12/2017 ............... A61K 8/44

OTHER PUBLICATIONS

Kostas D. Daskalakisl and George H. Nancollas. Dicalcium Phosphate Dihydrate Crystal Growth in The pH Region of 4.5 to 6.2. Mineral Scale Formation and Inhibition, New York: Springer Science+Business Media, 1995, 219-230. (Year: 1995).*
Google Search_pH of dicalcium phosphate dihydraate—Sep. 11, 2020 (Year: 2020).*
Google_patent_search_8-24-21_citric_acid_arginine_toothpaste.pdf (Year: 2021).*
Google_search_8-23-21_arginine_salts_in_toothpaste.pdf (Year: 2021).*
SciFinder_Search_CAS_93923-89-8_8-23-2021.pdf (Year: 2021).*
S. M. Berge, L. D. Highley, and D.C. Monkhouse. "Pharmaceutical Salts," J. Pharm. Sci., 66(1), Jan. 19, 1977. (Year: 1977).*
A. Wiegand, D. Bichsel, A. C. Magalhaes, K. Becker, T. Attin. Effect of sodium, amine and stannous fluoride at the same concentration and different pH on in vitro erosion. J. Dent. 37, 2009, 591-595). (Year: 2009).*
Anonymous, 2018, "Biocare Toothpaste", Mintel Database GNPD AN: 5669395.
Anonymous, 2018, "Original Flouride Toothpaste", Mintel Database GNPD AN: 5715235.
International Search Report and the Written Opinion of the International Searching Authority issued in International Application PCT/US2020/024545 dated Jul. 13, 2020.

* cited by examiner

*Primary Examiner* — Michael P Cohen

(57) ABSTRACT

This invention relates to oral care compositions, for example comprising a salt of a basic amino acid having a pH in solution of less than 7.5, an abrasive having a pH in solution of less than 7.5, and a fluoride ion source, and an acid selected from the group consisting of: a carboxylic acid (e.g., citric acid, lactic acid, glycolic acid, acetic acid, succinic acid, or fumaric acid), and an inorganic acid, wherein the inorganic acid is not phosphoric acid or sulfuric acid (e.g., wherein the inorganic acid is hydrochloric acid or sodium acid pyrophosphate), and to methods of using and of making these compositions.

5 Claims, No Drawings

ORAL CARE PRODUCT AND METHODS OF USE AND MANUFACTURE THEREOF

CROSS REFERENCE TO RELATED APPLICATIONS

This application claims priority to U.S. Provisional Application No. 62/825,952, filed on Mar. 29, 2019, the contents of which are incorporated herein by reference in its entirety.

FIELD OF THE INVENTION

This invention relates to oral care compositions, for example comprising an effective amount of a salt of a basic amino acid, wherein the salt is a salt of: (a) a carboxylic acid (e.g., citric acid, lactic acid, glycolic acid, acetic acid, succinic acid, or fumaric acid), or an inorganic acid, wherein the inorganic acid is not phosphoric acid or sulfuric acid (e.g., wherein the inorganic acid is hydrochloric acid or sodium acid pyrophosphate), and (b) a basic amino acid; an effective amount of a soluble fluoride salt, e.g., sodium fluoride, stannous fluoride or sodium monofluorophosphate, e.g., providing from about 100 to 25,000 ppm, e.g., about 750 to about 2000 ppm fluoride ions; a particulate material, e.g., natural calcium carbonate (NCC) (e.g., having an average particle size of 3-7 microns) or dicalcium phosphate (e.g., dicalcium phosphate dihydrate), which has a pH in an unbuffered solution of less than about 7.5, e.g., about 6.5 to about 7.4, e.g., about 6.8 to about 7.2, e.g., approximately neutral pH, and to methods of using and of making these compositions.

BACKGROUND OF THE INVENTION

Arginine and other basic amino acids are believed to have significant benefits in combating cavity formation and tooth sensitivity when used in oral care compositions. Combining these basic amino acids with minerals having oral care benefits, e.g., fluoride and calcium, to form an oral care product having acceptable long-term stability, however, has proven challenging. There have been various formulations issues with using amino acids in oral care compositions. For example, previously there had been the concern that the basic amino acid may raise the pH and facilitate dissociation of calcium ions that can react with fluoride ions to form an insoluble precipitate. And, moreover, that the higher pH has the potential to cause irritation.

At neutral pH or acidic pH, however, systems that utilize arginine bicarbonate may release carbon dioxide, leading to bloating and bursting of the containers. Moreover, it might be expected that lowering the pH to neutral or acidic conditions would reduce the efficacy of the formulation because the arginine may form an insoluble arginine-calcium complex that has a poorer affinity for the tooth surface, and moreover that lowering the pH would reduce any effect the formulation might have on buffering cariogenic lactic acid in the mouth. In order to lower the pH of the formulations, previous formulations that have sought to address these concerns have focused on acids such as phosphoric acid or sulfuric acid.

Accordingly, there is a need for a stable oral care product that provides a basic amino acid and also provides beneficial minerals such as fluoride and calcium.

BRIEF SUMMARY OF THE INVENTION

The invention encompasses oral care compositions and methods of using the same that are believed to be effective in inhibiting or reducing the accumulation of plaque, reducing levels of acid producing (cariogenic) bacteria, remineralizing teeth, and inhibiting or reducing gingivitis. The invention also encompasses compositions and methods to clean the oral cavity and provide improved methods of promoting oral health and/or systemic health, including cardiovascular health, e.g., by reducing potential for systemic infection via the oral tissues.

The invention thus comprises an oral care composition (a Composition of the Invention), e.g., a dentifrice, comprising
  i. an effective amount of a salt of a basic amino acid, wherein the salt is a salt of: (a) a carboxylic acid (e.g., citric acid, lactic acid, glycolic acid, acetic acid, succinic acid, or fumaric acid), or an inorganic acid, wherein the inorganic acid is not phosphoric acid or sulfuric acid (e.g., wherein the inorganic acid is hydrochloric acid or sodium acid pyrophosphate), and (b) a basic amino acid;
  ii. an effective amount of a soluble fluoride salt, e.g., sodium fluoride, stannous fluoride or sodium monofluorophosphate, e.g., providing from about 100 to 25,000 ppm, e.g., about 750 to about 2000 ppm fluoride ions;
  iii. a particulate material, e.g., natural calcium carbonate (NCC) (e.g., having an average particle size of 3-7 microns) or dicalcium phosphate (e.g., dicalcium phosphate dihydrate), which has a pH in an unbuffered solution of less than about 7.5, e.g., about 6.5 to about 7.4, e.g., about 6.8 to about 7.2, e.g., approximately neutral pH;

In one embodiment the invention encompasses a Composition of the Invention 1.0 (Composition 1.1), wherein the composition comprises
  i. an effective amount of a salt of a basic amino acid, wherein the salt is a salt of: (a) a carboxylic acid (e.g., citric acid, lactic acid, glycolic acid, acetic acid, succinic acid, or fumaric acid), or an inorganic acid, wherein the inorganic acid is not phosphoric acid or sulfuric acid (e.g., wherein the inorganic acid is hydrochloric acid or sodium acid pyrophosphate), and (b) a basic amino acid;
  ii. a salt of an inorganic acid and calcium (e.g., dicalcium phosphate) or calcium carbonate (e.g., natural calcium carbonate); and
  iii. an effective amount of a soluble fluoride salt; and
  iv. wherein the effective amount of a salt of a basic amino acid, e.g., arginine, e.g., is present in an amount of at least about 1%, for example about 1 to about 15%, having a pH in an unbuffered solution of less than about 7.5, e.g., about 6 to about 7.4, e.g., about 6.8 to about 7.2, e.g., approximately neutral pH.

The basic amino acid may be for example arginine. The fluoride salt may be for example sodium monofluorophosphate. Thus, Compositions of the Invention thus include a dentifrice comprising (i) arginine citrate, arginine lactate, arginine glycolate, arginine acetate, or arginine hydrochloride, (ii) dicalcium phosphate dihydrate or natural calcium carbonate, and (iii) sodium monofluorophosphate.

In another embodiment, the invention encompasses a Composition of the Invention (Composition 1.2) comprising
  i. an effective amount of a salt of a basic amino acid;
  ii. an effective amount of a soluble fluoride salt;
  iii. an anionic surfactant, e.g., sodium lauryl sulfate; and
  iv. wherein the salt of the basic amino acid is formed by the addition of an acid selected from the group consisting of: a carboxylic acid (e.g., citric acid, lactic acid, glycolic acid, acetic acid, succinic acid, or fumaric acid), or an inorganic acid, wherein the inorganic acid is not phosphoric acid or sulfuric acid (e.g., wherein the inorganic acid is hydrochloric acid or sodium acid pyrophosphate).

In another embodiment, the invention encompasses a Composition of the Invention (Composition 1.3) comprising
i. an effective amount of a salt of a basic amino acid;
ii. an effective amount of a soluble fluoride salt;
iii. an antibacterial agent;
iv. optionally, an anionic surfactant, e.g., sodium lauryl sulfate;
v. optionally, an anionic polymer, e.g., a copolymer of methyl vinyl ether and maleic anhydride; and
vi. wherein the salt of the basic amino acid is formed by the addition of an acid selected from the group consisting of: a carboxylic acid (e.g., citric acid, lactic acid, glycolic acid, acetic acid, succinic acid, or fumaric acid), or an inorganic acid, wherein the inorganic acid is not phosphoric acid or sulfuric acid (e.g., wherein the inorganic acid is hydrochloric acid or sodium acid pyrophosphate).

In another embodiment, the invention encompasses a Composition of the Invention (Composition 1.4) comprising
i. an effective amount of a salt of a basic amino acid;
ii. an effective amount of a soluble fluoride salt; and
iii. small particle abrasive having a RDA of about less than 160, e.g., about 40 to about 140, e.g., comprising at least about 5% of an abrasive having a d50 less than about 5 micrometers, e.g., silica having a d50 of about 3 to about 4 micrometers; and
iv. wherein the salt of the basic amino acid is formed by the addition of an acid selected from the group consisting of: a carboxylic acid (e.g., citric acid, lactic acid, glycolic acid, acetic acid, succinic acid, or fumaric acid), or an inorganic acid, wherein the inorganic acid is not phosphoric acid or sulfuric acid (e.g., wherein the inorganic acid is hydrochloric acid or sodium acid pyrophosphate).

In another embodiment, the invention encompasses a Composition of the Invention (Composition 1.5) comprising
i. an effective amount of a basic amino acid in free or salt form (e.g., arginine);
ii. an effective amount of a soluble fluoride salt, e.g., sodium fluoride, stannous fluoride or sodium monofluorophosphate, e.g., providing from about 100 to 25,000 ppm, e.g., about 750 to about 2000 ppm fluoride ions;
iii. an abrasive comprising, natural calcium carbonate (NCC) or dicalcium phosphate (e.g., dicalcium phosphate dihydrate), which has a pH in an unbuffered solution of less than about 7.5, e.g., about 6.5 to about 7.4, e.g., about 6.8 to about 7.2, e.g., approximately neutral pH; and
iv. an effective amount of a carboxylic acid (e.g., lactic acid, acetic acid, succinic acid, fumaric acid, citric acid, glycolic acid, or a combination thereof) and/or an inorganic acid, wherein the inorganic acid is not phosphoric acid or sulfuric acid (e.g., wherein the inorganic acid is hydrochloric acid or sodium acid pyrophosphate).

Composition 1.5 further encompasses an embodiment where the amount of carboxylic acid and/or inorganic acid, wherein the inorganic acid is not phosphoric acid or sulfuric acid, is sufficient to neutralize the basic amino acid (e.g., arginine).

In particular embodiments, the Compositions of the Invention are in the form of a dentifrice comprising additional ingredients selected from one or more of water, abrasives, surfactants, foaming agents, vitamins, polymers, enzymes, humectants, thickeners, antimicrobial agents, preservatives, flavorings, colorings and/or combinations thereof.

Without intending to be bound by a particular theory, it is hypothesized that a significant factor in the beneficial effect of arginine is that arginine and other basic amino acids can be metabolized by certain types of bacteria, e.g., *S. sanguis* which are not cariogenic and which compete with cariogenic bacteria such as *S. mutans*, for position on the teeth and in the oral cavity. The arginolytic bacteria can use arginine and other basic amino acids to produce ammonia, thereby raising the pH of their environment, while cariogenic bacteria metabolize sugar to produce lactic acid, which tends to lower the plaque pH and demineralize the teeth, ultimately leading to cavities. It is believed that regular use of a Composition of the Invention, over time, will lead to a relative increase in the arginolytic bacteria and a relative decrease in the cariogenic bacteria, resulting in a higher plaque pH (notwithstanding that the Composition of the Invention is itself generally pH neutral, the basic amino acid having been neutralized by a carboxylic acid or inorganic acid). It is believed that this pH-raising effect may be mechanistically separate from and complementary to the effect of fluoride in promoting remineralization and strengthening the tooth enamel.

The invention thus further encompasses methods to (i) reduce or inhibit formation of dental caries, (ii) reduce, repair or inhibit early enamel lesions, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat dry mouth, and/or (xiii) clean the teeth and oral cavity, comprising applying a Composition of the Invention to the oral cavity, e.g., by applying a Composition of the Invention to the oral cavity of a patient in need thereof.

DETAILED DESCRIPTION OF THE INVENTION

General Description

The invention thus comprises an oral care composition (Composition 1.0) comprising
i. an effective amount of a salt of a basic amino acid, wherein the salt is a salt of: (a) a carboxylic acid (e.g., citric acid, lactic acid, glycolic acid, acetic acid, succinic acid, or fumaric acid) or an inorganic acid, wherein the inorganic acid is not phosphoric acid or sulfuric acid (e.g., wherein the inorganic acid is hydrochloric acid or sodium acid pyrophosphate), and (b) a basic amino acid (e.g., arginine);
ii. an effective amount of a fluoride source, e.g., a soluble fluoride salt, e.g., sodium monofluorophosphate, providing from about 100 to 25,000 ppm fluoride ions, e.g., about 750 to about 2000 ppm;
iii. a particulate, e.g., dicalcium phosphate or natural calcium carbonate;

for example, any of the following compositions:

1.0.1. Composition 1.0, wherein the effective amount of a salt of a basic amino acid, e.g., arginine, e.g., is present in an amount of at least about 1%, for example about 1 to about 15%, e.g., having a pH in an unbuffered solution of less than about 7.5, e.g., about 6 to about 7.4, e.g., about 6.8 to about 7.2, e.g., approximately neutral pH.

1.0.2. Composition 1.0 or 1.0.1 wherein the basic amino acid is arginine, lysine, citrullene, omithine, creatine, histidine, diaminobutanoic acid, diaminoproprionic acid, salts thereof and/or combinations thereof.

1.0.3. Composition 1.0 or 1.0.1 or 1.0.2, wherein the basic amino acid has the L-configuration.

1.0.4. Any of the preceding compositions is provided in the form of a salt of a di- or tri-peptide comprising the basic amino acid (e.g., arginine).

1.0.5. Any of the preceding compositions wherein the basic amino acid is arginine.

1.0.6. Any of the preceding compositions wherein the basic amino acid is L-arginine.

1.0.7. Any of the preceding compositions wherein the carboxylic acid is selected from: citric acid, lactic acid, glycolic acid and acetic acid, succinic acid, fumaric acid, or a combination thereof.

1.0.8. Any of the preceding compositions wherein the inorganic acid that is not phosphoric acid or sulfuric acid, e.g., the inorganic acid is hydrochloric acid or sodium acid pyrophosphate when the particulate is natural calcium carbonate.

1.0.9. Any of the preceding compositions wherein the salt of the basic amino acid is arginine citrate.

1.0.10. Any of the preceding compositions wherein the salt of the basic amino acid is arginine lactate.

1.0.11. Any of the preceding compositions wherein the salt of the basic amino acid is arginine glycolate.

1.0.12. Any of the preceding compositions wherein the salt of the basic amino acid is arginine acetate.

1.0.13. Any of the preceding compositions wherein the salt of the basic amino acid is arginine hydrochloride.

1.0.14. Any of the preceding compositions wherein the salt of the basic amino acid is arginine hydrochloride, only when the particulate is calcium carbonate (e.g., natural calcium carbonate).

1.0.15. Any of the preceding compositions wherein the salt of the basic amino acid is formed in situ in the formulation by neutralization of the basic amino acid with an acid or a salt of an acid.

1.0.16. Any of the preceding compositions wherein the salt of the basic amino acid is formed by neutralization of the basic amino acid to form a premix prior to combination with the fluoride salt.

1.0.17. Any of the preceding compositions wherein the basic amino acid is present in an amount corresponding to about 0.1 to about 20%, e.g., about 1 wt. % to about 15 wt. %, of the total composition weight, the weight of the basic amino acid being calculated as free base form.

1.0.18. Composition 1.0.17 wherein the basic amino acid is present in an amount of about 7.5 wt. % of the total composition weight.

1.0.19. Composition 1.0.17 wherein the basic amino acid is present in an amount of about 5 wt. % of the total composition weight.

1.0.20. Composition 1.0.17 wherein the basic amino acid is present in an amount of about 3.75 wt. % of the total composition weight.

1.0.21. Composition 1.0.17 wherein the basic amino acid is present in an amount of about 1.5 wt. % of the total composition weight.

1.0.22. Any of the preceding compositions wherein the fluoride salt is stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.0.23. Any of the preceding compositions wherein the fluoride salt is a fluorophosphate.

1.0.24. Any of the preceding composition wherein the fluoride salt is sodium monofluorophosphate.

1.0.25. Any of the preceding compositions wherein the fluoride salt is present in an amount of about 0.01 wt. % to about 2 wt. % of the total composition weight.

1.0.26. Any of the preceding compositions wherein the soluble fluoride salt provides fluoride ion in an amount of about 0.1 to about 0.2 wt. % of the total composition weight.

1.0.27. Any of the preceding compositions wherein the soluble fluoride salt provides fluoride ion in an amount of from about 50 to 25,000 ppm.

1.0.28. Any of the preceding compositions which is a mouthwash having about 100 to about 250 ppm available fluoride ion.

1.0.29. Any of which is a dentifrice having about 750 to about 2000 ppm available fluoride ion.

1.0.30. Any of the preceding compositions wherein the composition comprises about 750 to about 2000 ppm fluoride ion.

1.0.31. Any of the preceding compositions wherein the composition comprises about 1000 to about 1500 ppm fluoride ion.

1.0.32. Any of the preceding compositions wherein the composition comprises about 1450 ppm fluoride ion.

1.0.33. Any of the preceding compositions wherein the pH is between about 6 and about 7.4.

1.0.34. Any of the preceding compositions wherein the pH is between about 6.8 and about 7.2.

1.0.35. Any of the preceding compositions wherein the pH is approximately neutral.

1.0.36. Any of the preceding compositions wherein the particular is an abrasive, and wherein the abrasive is selected from sodium bicarbonate, calcium phosphate (e.g., dicalcium phosphate dihydrate), calcium sulfate, natural calcium carbonate, precipitated calcium carbonate, silica (e.g., hydrated silica), iron oxide, aluminum oxide, perlite, plastic particles, e.g., polyethylene, and combinations thereof.

1.0.37. The immediately preceding composition wherein the abrasive or particulate is selected from a calcium phosphate (e.g., dicalcium phosphate dihydrate), calcium sulfate, natural calcium carbonate, precipitated calcium carbonate, silica (e.g., hydrated silica), and combinations thereof.

1.0.38. Any of the preceding compositions comprising an abrasive in an amount of about 15 wt. % to about 70 wt. % of the total composition weight.

1.0.39. Any of the preceding compositions comprising a small particle abrasive fraction of at least about 5% having a d50 of less than about 5 micrometers.

1.0.40. Any of the preceding compositions having a RDA of less than about 150, e.g., about 40 to about 140.

1.0.41. Any of the preceding compositions wherein the abrasive is natural calcium carbonate, and the natural calcium carbonate is present in an amount of 20%-60% by weight of the composition.

1.0.42. Any of the preceding compositions wherein the natural calcium carbonate is present in an amount of about 42%.

1.0.43. Any of the preceding compositions wherein the abrasive is dicalcium phosphate (e.g., dicalcium phosphate dihydrate), and the dicalcium phosphate (e.g., dicalcium phosphate dihydrate) is present in an amount of 20%-60% by weight of the composition.

1.0.44. Any of the preceding compositions wherein the dicalcium phosphate (e.g., dicalcium phosphate dihydrate) is present in an amount of about 40%.

1.0.45. Any of the preceding compositions comprising at least one surfactant.

1.0.46. Any of the preceding compositions comprising at least one surfactant selected from sodium lauryl sulfate, cocamidopropyl betaine, and combinations thereof.

1.0.47. Any of the preceding compositions comprising an anionic surfactant.

1.0.48. Any of the preceding compositions comprising sodium lauryl sulfate.

1.0.49. Any of the preceding compositions comprising at least one humectant.

1.0.50. Any of the preceding compositions comprising at least one humectant selected from glycerin, sorbitol and combinations thereof.

1.0.51. Any of the preceding compositions comprising at least one polymer.

1.0.52. Any of the preceding compositions comprising at least one polymer selected from polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum), and combinations thereof.

1.0.53. Any of the preceding compositions comprising gum strips or fragments.

1.0.54. Any of the preceding compositions comprising flavoring, fragrance and/or coloring.

1.0.55. Any of the preceding compositions comprising water.

1.0.56. Any of the preceding compositions comprising an antibacterial agent.

1.0.57. Any of the preceding compositions comprising an antibacterial agent selected from herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthom extract), bisguanide antiseptics (e.g., chlorhexidine, alexidine or octenidine), quatemary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.0.58. Any of the preceding compositions comprising an anti-inflammatory compound, e.g., an inhibitor of at least one of host pro-inflammatory factors selected from matrix metalloproteinases (MMP's), cyclooxygenases (COX), $PGE_2$, interleukin 1 (IL-1), IL-10 converting enzyme (ICE), transforming growth factor 131 (TGF-11), inducible nitric oxide synthase (iNOS), hyaluronidase, cathepsins, nuclear factor kappa B (NF-κB), and IL-1 Receptor Associated Kinase (IRAK), e,g, selected from aspirin, ketorolac, flurbiprofen, ibuprofen, naproxen, indomethacin, aspirin, ketoprofen, piroxicam, meclofenamic acid, nordihydoguaiaretic acid, and mixtures thereof.

1.0.59. Any of the preceding compositions comprising a whitening agent.

1.0.60. Any of the preceding compositions comprising a whitening agent selected from a whitening active selected from the group consisting of peroxides, metal chlorites, perborates, percarbonates, peroxyacids, hypochlorites, and combinations thereof.

1.0.61. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.0.62. Any of the preceding compositions comprising an antioxidant, e.g., selected from the group consisting of Co-enzyme Q10, PQQ, Vitamin D, Vitamin C, Vitamin E, Vitamin A, anethole-dithiothione, and mixtures thereof.

1.0.63. Any of the preceding composition comprising a $Zn^{2+}$ ion source, e.g., zinc citrate.

1.0.64. Any of the preceding compositions comprising an antibacterial agent in an amount of about 0.01 to about 5 wt. % of the total composition weight.

1.0.65. Any of the preceding compositions further comprising an agent that interferes with or prevents bacterial attachment, e.g., solbrol or chitosan.

1.0.66. Any of the preceding compositions further comprising an anti-calculus agent.

1.0.67. Any of the preceding compositions further comprising an anti-calculus agent which is a polyphosphate, e.g., pyrophosphate, tripolyphosphate, or hexametaphosphate, e.g., in sodium salt form.

1.0.68. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate.

1.0.69. Any of the preceding compositions further comprising a soluble calcium salt, e.g., selected from calcium sulfate, calcium chloride, calcium nitrate, calcium acetate, calcium lactate, and combinations thereof.

1.0.70. Any of the preceding compositions further comprising a physiologically acceptable potassium salt, e.g., potassium nitrate or potassium chloride, in an amount effective to reduce dentinal sensitivity.

1.0.71. Any of the preceding compositions comprising from about 0.1% to about 7.5% of a physiologically acceptable potassium salt, e.g., potassium nitrate and/or potassium chloride.

1.0.72. Any of the preceding compositions effective upon application to the oral cavity, e.g., with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity, (xiv) reduce erosion, (xv) whiten teeth, (xvi) immunize the teeth against cariogenic bacteria and/or (xvii) promote systemic health, including cardiovascular health, e.g., by reducing potential for systemic infection via the oral tissues.

1.0.73. A composition obtained or obtainable by combining the ingredients as set forth in any of the preceding compositions.

1.0.74. Any of the preceding compositions in a form selected from mouthrinse, toothpaste, tooth gel, tooth powder, non-abrasive gel, mousse, foam, mouth spray, lozenge, oral tablet, dental implement, chewing gum and pet care product.

1.0.75. Any of the preceding compositions wherein the composition is toothpaste.

1.0.76. Any of the preceding compositions wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.

1.0.77. Any of the preceding compositions 1.0-1.0.73 wherein the composition is a mouthwash.

1.0.78. Any of the preceding compositions, wherein the oral care composition comprises:
  a. purified water from 20-30% by wt.
  b. natural calcium carbonate from 35-45% by wt.
  c. sorbitol from 15-25% by wt.
  d. An anionic polymer (e.g., sodium lauryl sulfate) from 4%-7% by wt.
  e. A fluoride source (e.g., sodium monofluorophosphate) from 0.50%-1.25% by wt.
  f. Sodium bicarbonate from 0.05%-0.20% by wt.
  g. A silica thickening agent from 1%-3% by wt.
  h. An effective amount of a salt of arginine, wherein the salt is selected from the group consisting of: arginine citrate, arginine lactate, arginine acetate, arginine glycolate, and arginine hydrochloride.

1.0.79. Any of compositions 1.0-1.0.77, wherein the oral care composition comprises:
  a. Demineralized water from 30-35% by wt.
  b. Dicalcium phosphate dihydrate from 35-45% by wt.
  c. Glycerin from 15-20% by wt.
  d. An anionic polymer (e.g., sodium lauryl sulfate) from 0.75%-1.75% by wt.
  e. A fluoride source (e.g., sodium monofluorophosphate) from 0.75%-1.5% by wt.
  f. An alkali phosphate salt (e.g., tetrasodium pyrophosphate) from 0.15-0.50% by wt.
  g. A silica thickening agent (e.g., Zeodent-165) from 0.5%-1.5% by wt.
  h. An effective amount of a salt of arginine, wherein the salt is selected from the group consisting of: arginine citrate, arginine lactate, arginine acetate, arginine glycolate, and arginine hydrochloride.

Any of the preceding compositions, wherein the carboxylic acid, or inorganic acid, does not have a significant effect on arginine degradation relative to a control formula containing phosphoric acid.

Any of the preceding compositions, wherein the carboxylic acid, or inorganic acid, does has an improved effect on arginine degradation relative to a control formula containing phosphoric acid.

In one embodiment the invention encompasses an oral care composition (Composition 1.1), e.g., according to any of the preceding Compositions 1.0-1.0.71, comprising
  i. An effective amount of a salt of: (a) a carboxylic acid or an inorganic acid (e.g., wherein the inorganic acid is hydrochloric acid or sodium acid pyrophosphate), wherein the inorganic acid is not phosphoric acid or sulfuric acid; and (b) a basic amino acid,
  ii. a calcium salt or calcium carbonate; and
  iii. a soluble fluoride salt.

The invention thus comprises, e.g., the following embodiments of Composition 1.1:

1.1.1. Composition 1.1 wherein the acid which forms a salt with a basic amino acid is a carboxylic acid.

1.1.2. Composition 1.1 wherein the acid which forms a salt with a basic amino acid is an inorganic acid, wherein the inorganic acid is not phosphoric acid or sulfuric acid.

1.1.3. Composition 1.1.1 wherein the carboxylic acid is selected from: citric acid, lactic acid, glycolic acid and acetic acid, succinic acid, fumaric acid or a combination thereof.

1.1.4. Composition 1.1.2 wherein the inorganic acid that is not phosphoric acid or sulfuric acid, e.g., the inorganic acid is wherein the inorganic acid is hydrochloric acid or sodium acid pyrophosphate when the particulate is natural calcium carbonate.

1.1.5. Composition 1.1.2 wherein the inorganic acid that is not phosphoric acid or sulfuric acid is wherein the inorganic acid is hydrochloric acid or sodium acid pyrophosphate only when calcium carbonate is present.

1.1.6. Composition 1.1.2 wherein the salt of a carboxylic acid and a basic amino acid is selected from the: citrate salt, lactate salts, glycolate salt, and acetate salt.

1.1.7. Any of the foregoing compositions wherein the calcium salt is a salt of calcium and an inorganic acid.

1.1.8. Composition 1.1.9, wherein the calcium salt is a salt of calcium and inorganic oxoacid, e.g., calcium phosphate or calcium sulfate or mixtures thereof.

1.1.9. Any of the foregoing Compositions 1.1 et seq. wherein the basic amino acid is arginine, lysine, citrullene, omithine, creatine, histidine, diaminobutanoic acid, diaminoproprionic acid, salts thereof or combinations thereof.

1.1.10. Any of the foregoing Compositions 1.1 et seq. wherein the basic amino acid has the L-configuration.

1.1.11. Any of the foregoing Compositions 1.1 et seq. wherein the basic amino acid is arginine or a salt thereof.

1.1.12. Any of the foregoing Compositions 1.1 et seq. comprising an arginine salt selected from the group consisting of: arginine citrate, arginine lactate, arginine glycolate, arginine acetate, and arginine hydrochloride.

1.1.13. Any of the foregoing Compositions 1.1 et seq. wherein the fluoride salt is stannous fluoride, sodium fluoride, potassium fluoride, sodium monofluorophosphate, sodium fluorosilicate, ammonium fluorosilicate, amine fluoride, ammonium fluoride, and combinations thereof.

1.1.14. Any of the foregoing Compositions 1.1 et seq. wherein the fluoride source is a fluorophosphate.

1.1.15. Any of the preceding composition wherein the fluoride source is sodium monofluorophosphate.

1.1.16. Any of the foregoing Compositions 1.1 et seq. wherein the basic amino acid is present in an amount corresponding to about 1 wt. % to about 10 wt. % of the total composition weight, the weight of the basic amino acid being calculated as free base form.

1.1.17. Composition 1.1.16 wherein the basic amino acid is present in an amount of about 7.5 wt. % of the total composition weight.

1.1.18. Composition 1.1.16 wherein the basic amino acid is present in an amount of about 5 wt. % of the total composition weight.

1.1.19. Composition 1.1.16 wherein the basic amino acid is present in an amount of about 3.75 wt. % of the total composition weight.

1.1.20. Composition 1.1.16 wherein the basic amino acid is present in an amount of about 1.5 wt. % of the total composition weight.

1.1.21. Any of the foregoing Compositions 1.1 et seq. wherein the calcium salt is present in an amount of about 20 wt. % to about 60 wt. % of the total composition weight.

1.1.22. Any of the foregoing Compositions 1.1 et seq. wherein calcium phosphate is present in an amount of about 40 wt. % to about 50 wt. % of the total composition weight.

1.1.23. Any of the foregoing Compositions 1.1 et seq. wherein a citrate of the basic amino acid is formed by reaction with citric acid or citrate salts to provide an approximately neutral pH, e.g., about pH 6.8 to about pH 7.2.

1.1.24. Any of the foregoing Compositions 1.1 et seq. wherein a lactate of the basic amino acid is formed by reaction with lactic acid or lactate salts to provide an approximately neutral pH, e.g., about pH 6.8 to about pH 7.2.

1.1.25. Any of the foregoing Compositions 1.1 et seq. wherein a glycolate of the basic amino acid is formed by reaction with glycolic acid or glycolate salts to provide an approximately neutral pH, e.g., about pH 6.8 to about pH 7.2.

1.1.26. Any of the foregoing Compositions 1.1 et seq. wherein an acetate of the basic amino acid is formed by reaction with acetic acid, succinic acid, fumaric acid or acetate salts to provide an approximately neutral pH, e.g., about pH 6.8 to about pH 7.2.

1.1.27. Any of the foregoing Compositions 1.1 et seq. wherein a hydrochloride of the basic amino acid is formed by reaction with hydrochloride salts to provide an approximately neutral pH, e.g., about pH 6.8 to about pH 7.2.

1.1.28. Any of the foregoing Compositions 1.1 et seq. wherein the fluoride salt is present in an amount of about 0.01 wt. % to about 2 wt. % of the total composition weight.

1.1.29. Any of the foregoing Compositions 1.1 et seq. wherein the fluoride salt provides fluoride ion in an amount of about 0.1 to about 0.2 wt. % of the total composition weight.

1.1.30. Any of the foregoing Compositions 1.1 et seq., e.g., in the form of a dentifrice, wherein the composition comprises about 500 to about 15,000 ppm fluoride ion.

1.1.31. Any of the foregoing Compositions 1.1 et seq. wherein the composition comprises about 1000 to about 1500 ppm fluoride ion.

1.1.32. Any of the foregoing Compositions 1.1 et seq. wherein the composition comprises about 1450 ppm fluoride ion.

1.1.33. Any of the foregoing Compositions 1.1 et seq. wherein the pH is less than about 7.5.

1.1.34. Any of the preceding compositions wherein the pH is between about 6 and about 7.3.

1.1.35. Any of the foregoing Compositions 1.1 et seq. wherein the pH is between about 6.8 and about 7.2.

1.1.36. Any of the foregoing Compositions 1.1 et seq. effective upon application to the oral cavity, e.g., with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) reduce dry mouth, (xiii) clean the teeth and oral cavity (xiv) reduce erosion, (xv) whiten teeth, and/or (xvi) immunize the teeth against cariogenic bacteria.

1.1.37. Any of the foregoing Compositions 1.1 et seq. comprising the salt of a basic amino acid, a phosphate abrasive material or calcium carbonate, and a fluorophosphate.

1.1.38. Any of the foregoing Compositions 1.1 et seq. comprising an arginine salt (e.g, arginine citrate, arginine lactate, arginine glycolate, arginine acetate, or arginine hydrochloride), dicalcium phosphate dihydrate or natural calcium carbonate, and sodium monofluorophosphate.

1.1.39. Any of the foregoing Compositions 1.1 et seq. obtained or obtainable by the steps of combining a basic amino acid with a carboxylic acid or inorganic acid that is not phosphoric or sulfuric acid, or a salt selected from citrate, lactate, glycolate, acetate, and hydrochloride, or a combination thereof to obtain a pH of about 7 to form a premix, which is used to make the desired composition.

1.1.40. Any of the foregoing Compositions 1.1 et seq. obtained or obtainable by the steps of combining a basic amino acid with a carboxylic acid or inorganic acid that is not phosphoric or sulfuric acid, or a salt selected from citrate, lactate, glycolate, acetate, and hydrochloride, or a combination thereof, to obtain a pH of about 7 to form a premix, and combining the premix with dicalcium phosphate or natural calcium carbonate, and a fluoride ion source.

1.1.41. Any of the foregoing Compositions 1.1 et seq. obtained or obtainable by any of Method 2, et seq. as hereinafter set forth.

1.1.42. A composition obtained or obtainable by combining the ingredients as set forth in any of the preceding compositions.

1.1.43. Any of the foregoing Compositions 1.1 et seq. wherein the composition is toothpaste.

1.1.44. Composition 1.1.45 wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.

1.1.45. Any of the foregoing Compositions 1.1-1.1.44 wherein the composition is a mouthwash.

In another embodiment, the invention encompasses a Composition of the Invention (Composition 1.2), e.g., according to any of the preceding Compositions 1.0-1.0.71, comprising
  i. An effective amount of a salt of: (a) carboxylic acid or an inorganic acid, wherein the inorganic acid is not phosphoric acid or sulfuric acid; and (b) a basic amino acid;
  ii. an effective amount of a soluble fluoride salt;
  iii. an anionic surfactant, e.g., sodium lauryl sulfate.

In another embodiment, the invention encompasses a Composition of the Invention (Composition 1.3) e.g., according to any of the preceding Compositions 1.0-1.0.71, comprising
  i. An effective amount of a salt of: (a) carboxylic acid or an inorganic acid, wherein the inorganic acid is not phosphoric acid or sulfuric acid; and (b) a basic amino acid;
  ii. an effective amount of a soluble fluoride salt;
  iii. an anionic surfactant, e.g., sodium lauryl sulfate;
  iv. an anionic polymer, e.g., a copolymer of methyl vinyl ether and maleic anhydride; and In another embodiment, the invention encompasses a Composition of the Invention (Composition 1.4) e.g., according to any of the preceding Compositions 1.0-1.0.71, comprising
  i. An effective amount of a salt of: (a) carboxylic acid or an inorganic acid, wherein the inorganic acid is not phosphoric acid or sulfuric acid; and (b) a basic amino acid;
  ii. an effective amount of a soluble fluoride salt; and
  iii. a particulate material, (e.g., calcium carbonate, e.g., natural or precipitated calcium carbonate) the composition having an RDA of less than about 160, e.g., about 40 to about 140, e.g., comprising at least about 5% of a particulate having a d50 less than about 5 micrometers, e.g., silica having a d50 of about 3 to about 4 micrometers.

In another embodiment, the invention encompasses a Composition of the Invention (Composition 1.5) which is an oral care composition comprising
  i. an effective amount of a basic amino acid in free or salt form (e.g., arginine);
  ii. an effective amount of a soluble fluoride salt, e.g., sodium fluoride, stannous fluoride or sodium monofluorophosphate, e.g., providing from about 100 to 25,000 ppm, e.g., about 750 to about 2000 ppm fluoride ions;
  iii. an abrasive, e.g., natural calcium carbonate (NCC) or dicalcium phosphate (e.g., dicalcium phosphate dihydrate), which has a pH in an unbuffered solution of less than about 7.5, e.g., about 6.5 to about 7.4, e.g., about 6.8 to about 7.2, e.g., approximately neutral pH; and
  iv. an effective amount of a carboxylic acid (e.g., lactic acid, acetic acid, succinic acid, fumaric acid, citric acid, glycolic acid, or a combination thereof) and/or an inorganic acid, wherein the inorganic acid is not phosphoric acid or sulfuric acid (e.g., wherein the inorganic acid is hydrochloric acid or sodium acid pyrophosphate).

The invention thus comprises, e.g., the following embodiments of Composition 1.5:
1.5.1. Composition 1.5 wherein the basic amino acid is arginine, lysine, citrulline, ornithine, creatine, histidine, diaminobutanoic acid, diaminoproprionic acid, salts thereof and/or combinations thereof.
1.5.2. Composition 1.5 or 1.5.1, wherein the basic amino acid has the L-configuration.
1.5.3. Any of the preceding compositions is provided in the form of a salt of a di- or tri-peptide comprising the basic amino acid.
1.5.4. Any of the preceding compositions wherein the basic amino acid is arginine, e.g., L-arginine.
1.5.5. Any of the preceding compositions wherein the basic amino acid is partially or wholly in salt form.
1.5.6. Any of the preceding compositions wherein the carboxylic acid is selected from: citric acid, lactic acid, glycolic acid and acetic acid, succinic acid, or fumaric acid.
1.5.7. Any of the preceding compositions wherein the inorganic acid that is not phosphoric acid or sulfuric acid is hydrochloric acid or sodium acid pyrophosphate, e.g., where the inorganic acid hydrochloric acid or sodium acid pyrophosphate when the particulate is natural calcium carbonate.
1.5.8. Composition 1.1.2 wherein the inorganic acid that is not phosphoric acid or sulfuric acid is wherein the inorganic acid is hydrochloric acid or sodium acid pyrophosphate only when natural calcium carbonate is present.
1.5.9. Any of the preceding compositions wherein the basic amino acid comprises arginine citrate.
1.5.10. Any of the preceding compositions wherein the basic amino acid comprises arginine hydrochloride.
1.5.11. Any of the preceding compositions wherein the basic amino acid comprises arginine lactate.
1.5.12. Any of the preceding compositions wherein the basic amino acid comprises arginine glycolate.
1.5.13. Any of the preceding compositions wherein the basic amino acid comprises arginine acetate.
1.5.14. Any of the preceding compositions wherein the salt of the basic amino acid is formed in situ in the formulation by neutralization of the basic amino acid with an acid or a salt of an acid.
1.5.15. Any of the preceding compositions wherein the salt of the basic amino acid is formed by neutralization of the basic amino acid to form a premix prior to combination with the fluoride salt.
1.5.16. Any of the preceding compositions wherein the amount of the carboxylic acid, and/or the amount of inorganic acid that is not phosphoric acid or sulfuric acid, is effective to neutralize the basic amino acid.
1.5.17. Any of the preceding compositions wherein the amount of the carboxylic acid, and/or the amount of inorganic acid that is not phosphoric acid or sulfuric acid, is from 0.5 wt %-1.1 wt % (e.g., 0.60%, 0.80%, or 1.0%) by weight of the composition.
1.5.18. Any of the preceding compositions wherein the basic amino acid is present in an amount corresponding to 1% to 15% of the total composition weight, the weight of the basic amino acid being calculated as free base form.
1.5.19. Any of the preceding compositions wherein the basic amino acid is present in an amount corresponding 8% to 10% of the total composition weight, the weight of the basic amino acid being calculated as free base form.

1.5.20. Any of the preceding compositions wherein the abrasive is selected from sodium bicarbonate, calcium phosphate (e.g., dicalcium phosphate dihydrate), calcium sulfate, natural calcium carbonate, precipitated calcium carbonate, silica (e.g., hydrated silica), iron oxide, aluminum oxide, perlite, plastic particles, e.g., polyethylene, and combinations thereof.

1.5.21. The immediately preceding composition wherein the abrasive is selected from a calcium phosphate (e.g., dicalcium phosphate dihydrate), calcium sulfate, natural calcium carbonate, precipitated calcium carbonate, silica (e.g., hydrated silica), and combinations thereof.

1.5.22. Any of the preceding compositions comprising an abrasive in an amount of about 15 wt. % to about 70 wt. % of the total composition weight.

1.5.23. Any of the preceding compositions comprising a small particle abrasive fraction of at least about 5% having a d50 of less than about 5 micrometers.

1.5.24. Any of the preceding compositions having a RDA of less than about 150, e.g., about 40 to about 140.

1.5.25. Any of the preceding compositions wherein the abrasive is natural calcium carbonate, and the natural calcium carbonate is present in an amount of 20%-60% by weight of the composition.

1.5.26. Any of the preceding compositions wherein the natural calcium carbonate is present in an amount of about 42%.

1.5.27. Any of the preceding compositions wherein the abrasive is dicalcium phosphate (e.g., dicalcium phosphate dihydrate), and the dicalcium phosphate (e.g., dicalcium phosphate dihydrate) is present in an amount of 20%-60% by weight of the composition.

1.5.28. Any of the preceding compositions wherein the dicalcium phosphate (e.g., dicalcium phosphate dihydrate) is present in an amount of about 40%.

1.5.29. Any of the preceding compositions comprising at least one surfactant.

1.5.30. Any of the preceding compositions comprising at least one surfactant selected from sodium lauryl sulfate, cocamidopropyl betaine, and combinations thereof.

1.5.31. Any of the preceding compositions comprising an anionic surfactant.

1.5.32. Any of the preceding compositions comprising sodium lauryl sulfate.

1.5.33. Any of the preceding compositions comprising at least one humectant.

1.5.34. Any of the preceding compositions comprising at least one humectant selected from glycerin, sorbitol and combinations thereof.

1.5.35. Any of the preceding compositions effective upon application to the oral cavity, e.g., with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity, (xiv) reduce erosion, (xv) whiten teeth, (xvi) immunize the teeth against cariogenic bacteria and/or (xvii) promote systemic health, including cardiovascular health, e.g., by reducing potential for systemic infection via the oral tissues.

1.5.36. A composition obtained or obtainable by combining the ingredients as set forth in any of the preceding compositions.

1.5.37. Any of the preceding compositions, wherein the composition is an oral care composition in a form selected from mouthrinse, toothpaste, tooth gel, tooth powder, non-abrasive gel, mousse, foam, mouth spray, lozenge, oral tablet, dental implement, chewing gum and pet care product.

1.5.38. Any of the preceding compositions wherein the composition is toothpaste.

1.5.39. Any of the preceding compositions wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.

1.5.40. Any of the preceding compositions 1.5-1.5.37 wherein the composition is a mouthwash.

1.5.41. Any of the preceding compositions, wherein the oral care composition comprises:
  a. purified water from 20-30% by wt.
  b. natural calcium carbonate from 35-45% by wt.
  c. sorbitol from 15-25% by wt.
  d. Sodium lauryl sulfate from 4%-7% by wt.
  e. Sodium monofluorophosphate from 0.50%-1.25% by wt.
  f. Sodium bicarbonate from 0.05%-0.20% by wt.
  g. A silica thickening agent from 1%-3% by wt.
  h. L-arginine from 1.0-2.0% by wt; and
  i. An acid from 0.25%-1.0% by wt., wherein the acid is selected from the group consisting of: citric acid, lactic acid, glycolic acid, acetic acid, succinic acid, fumaric acid, hydrochloric acid, sodium acid pyrophosphate, and combinations thereof.

1.5.42. Any of compositions 1.5-1.5.40, wherein the oral care composition comprises:
  a. Demineralized water from 30-35% by wt.
  b. Dicalcium phosphate dihydrate from 35-45% by wt.
  c. Glycerin from 15-20% by wt.
  d. Sodium lauryl sulfate from 0.75%-1.75% by wt.
  e. Sodium monofluorophosphate from 0.75%-1.5% by wt.
  f. Tetrasodium pyrophosphate from 0.15-0.50% by wt.
  g. Zeodent-165 from 0.5%-1.5% by wt.
  h. L-arginine from 1.0-2.0% by wt; and
  i. An acid from 0.5%-1.25% by wt., wherein the acid is selected from the group consisting of: citric acid, lactic acid, glycolic acid, acetic acid, succinic acid, fumaric acid, hydrochloric acid and sodium acid pyrophosphate.

1.5.43. Any of the preceding compositions, wherein the carboxylic acid, or inorganic acid, does not have a significant effect on arginine degradation relative to a control formula containing phosphoric acid.

1.5.44. Any of the preceding compositions, wherein the carboxylic acid, or inorganic acid, does has an improved effect on arginine degradation relative to a control formula containing phosphoric acid.

In another embodiment, the invention encompasses a method (Method 2) for preparing an oral composition, e.g., any Compositions under 1.0, 1.1, 1.2, 1.3, 1.4, or 1.5 supra, comprising
  i. forming a premix by combining a basic amino acid in a gel phase with an acid and/or salt thereof to obtain a pH of less than about 7.5, and ii. combining the premix with other ingredients of the formulation, including a soluble fluoride salt.

Method 2 thus comprises, e.g., the following embodiments:

2.1. Method 2 wherein the acid combined with the basic amino acid is a carboxylic acid or an inorganic acid, wherein the organic acid is not phosphoric acid or sulfuric acid.
2.2. Method 2.1 wherein the acid is citric acid, lactic acid, glycolic acid, acetic acid, succinic acid, fumaric acid, hydrochloric acid sodium acid pyrophosphate, or any combination thereof.
2.3. Method 2.2, wherein the acid is hydrochloric acid or sodium acid pyrophosphate only when the other ingredients include calcium carbonate (e.g., natural calcium carbonate) as an abrasive.
2.4. Any of the preceding methods wherein the other ingredients of the formulation comprise a calcium phosphate salt or calcium carbonate (e.g., natural calcium carbonate or precipitated calcium carbonate).
2.5. The preceding method wherein the calcium phosphate is dicalcium phosphate dihydrate.
2.6. Any of the preceding methods wherein the fluoride salt is selected from stannous fluoride, sodium fluoride, potassium fluoride, sodium monofluorophosphate, sodium fluorosilicate, ammonium fluorosilicate, amine fluoride, ammonium fluoride, and combinations thereof.
2.7. Any of the preceding methods wherein the fluoride salt is a fluorophosphate.
2.8. Any of the preceding methods wherein the fluoride salt is sodium monofluorophosphate.
2.9. Any of the preceding methods wherein the basic amino acid is selected from arginine, lysine, citrullene, ornithine, creatine, histidine, diaminobutanoic acid, diaminopropionic acid, salts and combinations thereof.
2.10. Any of the preceding methods wherein the basic amino acid has the L-configuration.
2.11. Any of the preceding methods wherein the basic amino acid is arginine.
2.12. Any of the preceding methods wherein the premix has a pH of about 6 to about 7.3.
2.13. Any of the preceding methods wherein the premix has a pH of about 6.8 to about 7.2.
2.14. Any of the preceding methods wherein the premix has a pH of about 7.
2.15. Any of the preceding methods when carried out at room temperature and pressure.
2.16. Any of the preceding methods wherein the ingredients and their respective amounts are as set forth in any of the embodiments as set forth under Compositions 1.0, 1.1, 1.2, 1.3 or 1.4.
2.17. Any of the preceding compositions, wherein the carboxylic acid, or inorganic acid, does not have a significant effect on arginine degradation relative to a control formula containing phosphoric acid.
2.18. Any of the preceding compositions, wherein the carboxylic acid, or inorganic acid, does has an improved effect on arginine degradation relative to a control formula containing phosphoric acid.

In another embodiment, the invention encompasses a method (Method 3) to improve oral health comprising applying an effective amount of the oral composition of any of the embodiments under Compositions 1.0, 1.1, 1.2, 1.3 1.4, or 1.5, et seq. to the oral cavity of a subject in need thereof, e.g., a method to i. reduce or inhibit formation of dental caries,
ii. reduce, repair or inhibit early enamel lesions, e.g., as detected by quantitative light-induced fluorescence (QLF) or electrical caries measurement (ECM),
iii. reduce or inhibit demineralization and promote remineralization of the teeth,
iv. reduce hypersensitivity of the teeth,
v. reduce or inhibit gingivitis,
vi. promote healing of sores or cuts in the mouth,
vii. reduce levels of acid producing bacteria,
viii. to increase relative levels of arginolytic bacteria,
ix. inhibit microbial biofilm formation in the oral cavity,
x. raise and/or maintain plaque pH at levels of at least pH 5.5 following sugar challenge,
xi. reduce plaque accumulation,
xii. treat, relieve or reduce dry mouth,
xiii. clean the teeth and oral cavity,
xiv. reduce erosion,
xv. whiten teeth,
xvi. immunize the teeth against cariogenic bacteria; and/or
xvii. promote systemic health, including cardiovascular health, e.g., by reducing potential for systemic infection via the oral tissues.

The invention further comprises the use of arginine in the manufacture of a Composition of the Invention, e.g., for use in any of the indications set forth in Method 3.

The invention further provides an oral care composition of any of Compositions 1.0, 1.1, 1.2, 1.3, 1.4, 1.5 et seq, for use in the treatment of at least one of demineralized teeth and enamel lesions within an oral cavity of a subject, or for enhancing the mineralization of teeth within an oral cavity of a subject.

The invention further provides the use of an oral care composition of any of Compositions 1.0, 1.1, 1.2, 1.3, 1.4, 1.5 et seq for the manufacture of a medicament for enhancing the mineralization of teeth within an oral cavity of a subject.

The invention further provides a method of mineralizing at least one of demineralized teeth and enamel lesions within an oral cavity of a subject, the method comprising treating the oral cavity with an oral care composition of any of Compositions 1.0, 1.1, 1.2, 1.3, 1.4, 1.5 et seq.

The invention further provides an oral care composition comprising a salt of a basic amino acid neutralized by a carboxylic acid or inorganic acid, wherein the acid is not phosphoric or sulfuric acid, for reducing or inhibiting the formation of dental caries by increasing the pH of plaque in an oral cavity of a subject when treated with the oral composition.

The invention further provides the use of a salt of a basic amino acid neutralized by a carboxylic acid or inorganic acid, wherein the acid is not phosphoric or sulfuric acid, in an oral care composition for reducing or inhibiting the formation of dental caries by increasing the pH of plaque in an oral cavity of a subject when treated with the oral composition, and the use of a salt of a basic amino acid neutralized by a carboxylic acid, or inorganic acid, wherein the inorganic acid is not phosphoric or sulfuric acid, for the manufacture of a medicament for use in reducing or inhibiting the formation of dental caries by increasing the pH of plaque in an oral cavity of a subject treated with the medicament.

The invention further provides a method of increasing the pH of plaque in an oral cavity of a subject, the method comprising treating the oral cavity with an oral care composition comprising a salt of a basic amino acid neutralized by a carboxylic acid or inorganic acid, wherein the inorganic acid is not phosphoric or sulfuric acid.

The invention further provides an oral care composition comprising a salt of a basic amino acid and a carboxylic acid, or inorganic acid, wherein the acid is not phosphoric or sulfuric acid, a soluble fluoride salt and a calcium salt of an inorganic acid.

The invention further provides an oral care composition comprising a soluble fluoride salt and a calcium salt of an inorganic acid, and, in addition, a salt of a basic amino acid and a carboxylic acid or inorganic acid, wherein the salt of the basic amino acid is not made by using phosphoric or sulfuric acid, for increasing the stability of the fluoride in the composition.

The invention further provides a method of producing an oral care composition, the method comprising the steps of:
  i. providing a basic amino acid and a carboxylic acid or inorganic acid, wherein the acid is not phosphoric or sulfuric acid, and neutralizing the basic amino acid with the carboxylic acid or inorganic acid, wherein the acid is not phosphoric or sulfuric acid, to form a salt of the basic amino acid, e.g., where the acid is added to the basic amino acid (e.g., arginine) directly to a gel tank or mixing tank;
  ii. combining the salt of the basic amino acid with at least a soluble fluoride salt and a calcium salt of an inorganic acid to form the oral care composition.

The invention further provides a method of producing an oral care composition, the method comprising the step of: combining together a basic amino acid component, a soluble fluoride salt and a calcium salt of an inorganic acid, wherein for increasing the stability of the fluoride in the composition, the basic amino acid is neutralized with a carboxylic acid or inorganic acid, wherein the acid is not phosphoric or sulfuric acid to form a salt of the basic amino acid prior to the combining step.

The invention further provides the use, in an oral care composition, of a salt of a basic amino acid, the salt being formed by neutralizing the basic amino acid with a carboxylic acid, or inorganic acid, wherein the acid is not phosphoric or sulfuric acid, as an additive for an oral care composition, comprising at least a soluble fluoride salt and a calcium salt of an inorganic acid, for increasing the stability of the fluoride in the composition.

It may therefore be seen by the skilled practitioner in the oral care art that a number of different yet surprising technical effects and advantages can result from the formulation, and use, of an oral care composition, for example a dentifrice, in accordance with one or more aspects of the invention, which are directed to the provision of different combinations of active components or ingredients, and preferably their respective amounts, within the composition.

Levels of active ingredients will vary based on the nature of the delivery system and the particular active. For example, the basic amino acid may be present at levels from, e.g., about 0.1 to about 20 wt % (expressed as weight of free base), e.g., about 0.1 to about 3 wt % for a mouthrinse, about 1 to about 10 wt % for a consumer toothpaste or about 7 to about 20 wt % for a professional or prescription treatment product. Fluoride may be present at levels of, e.g., about 25 to about 25,000 ppm, for example about 25 to about 250 ppm for a mouthrinse, about 750 to about 2,000 ppm for a consumer toothpaste, or about 2,000 to about 25,000 ppm for a professional or prescription treatment product. Levels of antibacterial will vary similarly, with levels used in toothpaste being e.g., about 5 to about 15 times greater than used in mouthrinse.

Basic Amino Acids

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, citrullene, omithine, creatine, histidine, diaminobutanoic acid, diaminoproprionic acid, salts thereof or combinations thereof. In a particular embodiment, the basic amino acids are selected from arginine, citrullene, and omithine.

In certain embodiments, the basic amino acid is arginine, for example, 1-arginine, or a salt thereof.

In some embodiments the basic amino acid comprises at least one intermediate produced in the arginine deiminase system. The intermediates produced in the arginine deiminase system may be useful in an oral care composition to provide plaque neutralization for caries control and/or prevention. Arginine is a natural basic amino acid that may be found in the oral cavity. Arginine in the mouth may be utilized by certain dental plaque bacterial strains such as *S. sanguis, S. gordonii, S. parasanguis, S. rattus, S. milleri, S. anginosus, S. faecalis, A. naeslundii, A. odonolyticus, L. cellobiosus, L. brevis, L. fermentum, P. gingivalis,* and *T. denticola* for their survival. Such organisms may perish in an acidic environment that may be present at areas close to the tooth surface where acidogenic and aciduric cariogenic strains may use sugars to produce organic acids. Thus, these arginolytic strains may break down arginine to ammonia to provide alkalinity to survive and, in addition, buffer the plaque and make a hostile environment for the cariogenic systems.

Such arginolytic organisms may catabolize arginine by an internal cellular enzyme pathway system called the "arginine deiminase system" whereby intermediates in the pathway are formed. In this pathway, L-arginine may be broken down to L-citrulline and ammonia by arginine deiminase. L-citrulline may then be broken down by omithane trancarbamylase in the presence of inorganic phosphate to L-omithine and carbamyl phosphate. Carbamate kinase may then break down carbamyl phosphate to form another molecule of ammonia and carbon dioxide, and in the process also forms ATP (adenosine 5'-triphosphate). ATP may be used by the arginolytic bacteria as an energy source for growth. Accordingly, when utilized, the arginine deiminase system may yield two molecules of ammonia.

It has been found that, in some embodiments, the ammonia may help in neutralizing oral plaque pH to control and/or prevent dental caries.

The oral care composition of some embodiments of the present invention may include intermediates produced in the arginine deiminase system. Such intermediates may include citrulline, omithine, and carbamyl phosphate. In some embodiments, the other care composition includes citrulline. In some embodiments, the oral care composition includes omithine. In some embodiments, the oral care composition includes carbamyl phosphate. In other embodiments, the oral care composition includes any combination of citrulline, omithine, carbamyl phosphate, and/or other intermediates produced by the arginine deiminase system.

The oral care composition may include the above described intermediates in an effective amount. In some embodiments, the oral care composition includes about 1 mmol/L to about 10 mmol/L intermediate. In other embodiments, the oral care composition includes about 3 mmol/L to about 7 mmol/L intermediate. In other embodiments, the oral care composition includes about 5 mmol/L intermediate.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

In various embodiments, the basic amino acid is present in an amount of about 0.5 wt. % to about 20 wt. % of the total composition weight, about 1 wt. % to about 15 wt. % of the total composition weight, for example about 1.5 wt. %, about 3.75 wt. %, about 5 wt. %, or about 7.5 wt. %, or about 10 wt % of the total composition weight.

Carboxylic Acids, Inorganic Acids, and their Salts

The term "carboxylic acid" refers to an organic compound that contains a carboxyl group (C(=O)OH). The general formula of a carboxylic acid is R—COOH, with R referring to the rest of the (possibly quite large) molecule. Carboxylic acids can include, but are not limited to, glycolic acid, lactic acid, acetic acid, succinic acid, fumaric acid and citric acid. Carboxylic acids can also include, but are not limited to, alpha hydroxy acids. Alpha hydrolic acids, can include, but are not limited to, glycolic acid, lactic acid, and citric acid.

Salts and esters of carboxylic acids are called carboxylates. When a carboxyl group is deprotonated, its conjugate base forms a carboxylate anion. Carboxylic acids within the scope of the present invention include, but are not limited to, glycolic acid, lactic acid, acetic acid, succinic acid, fumaric acid and citric acid.

The term "inorganic acid" refers to acids which do not contain carbon, e.g., mineral acids, e.g., wherein the inorganic acid is hydrochloric acid or sodium acid pyrophosphate. In a particular embodiment, the inorganic acid is an "inorganic which is not phosphoric acid or sulfuric acid", which refers to inorganic acids, such as hydrochloric acid or sodium acid pyrophosphate.

In certain embodiments, the Compositions of the Invention are substantially free of organic phosphates, e.g., alkyl phosphates or phytates and/or are substantially free of carbonates or bicarbonates. By "substantially free" is meant, in this context, present if at all in amounts of less than 5%, e.g., less than 1% relative to the inorganic acid or inorganic oxoacid.

Inorganic acids within the scope of the present invention include, but are not limited to, hydrochloric acid or sodium acid pyrophosphate. In some embodiments, the acid to form a salt with the calcium is provided in the form of another salt, e.g., a phosphate. Salts thereof for use in the present invention to neutralize the basic amino acid are those having relatively high solubility, e.g., alkali salts and ammonium salts which are capable of buffering the basic amino acid to a pH of below about 7.5.

The carboxylic acid and inorganic acids are present in an amount to neutralize the calcium and the basic amino acid sufficiently so as to provide an approximately neutral pH, e.g., pH about 6.8 to about 7.2.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference.

Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

In certain embodiments, the oral care composition of the invention may also contain a source of fluoride ions or fluorine-providing ingredient in amounts sufficient to supply about 25 ppm to 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A mouthwash, for example, would typically have about 100 to about 250 ppm fluoride. A toothpaste for general consumer use would typically have about 1000 to about 1500 ppm, with pediatric toothpaste having somewhat less. A dentifrice or coating for professional application could have as much as 5,000 or even 25,000 ppm fluoride.

Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Particulates and Abrasives

The Compositions of the Invention may comprise a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate. Alternatively, calcium carbonate, and in particular natural calcium carbonate or precipitated calcium carbonate, may be employed as an abrasive.

The compositions may include one or more additional particulate materials, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof.

The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In certain embodiments, abrasive materials useful in the practice of the oral care compositions in accordance with the invention include silica gels and precipitated amorphous silica having an oil absorption value of about less than 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns.

In particular embodiments, the particulate or abrasive materials comprise a large fraction of very small particles, e.g., having a d50 less than about 5 microns, for example small particle silica (SPS) having a d50 of about 3 to about 4 microns, for example Sorbosil AC43® (Ineos). Such small particles are particularly useful in formulations targeted at reducing hypersensitivity. The small particle component may be present in combination with a second larger particle abrasive. In certain embodiments, for example, the formulation comprises about 3 to about 8% SPS and about 25 to about 45% of a conventional abrasive.

Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of about 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

In some embodiments the basic amino acid is incorporated into a dentifrice composition having a base formulation comprising calcium carbonate, and in particular natural calcium carbonate or precipitated calcium carbonate, as an abrasive. L-arginine and arginine salts such as arginine bicarbonate are themselves distinctly bitter in taste, and in aqueous solution can also impart a fishy taste. Consequently, it was expected that when L-arginine or arginine salts were incorporated into oral care products such as dentifrice formulations at effective concentrations to impart anticavity efficacy and sensitivity relief, typically in an amount of from 2 to 10 wt % based on the total weight of the dentifrice formulation, the taste and mouthfeel of the dentifrice formulations would be degraded as compared to the same formulation without the addition of L-arginine or arginine salts.

Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g. about 5.5 microns. Because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a $D_{90}$ of 3-6 microns, for example 3.8=4.9, e.g., about 4.3; a $D_{50}$ of 1-4 microns, e.g. 2.2-2.6 microns, e.g., about 2.4 microns, and a $D_{10}$ of 1-2 microns, e.g., 1.2-1.4, e.g. about 1.3 microns. The particles have relatively high-water absorption, e.g., at least 25 g/100 g, e.g. 30-70 g/100 g. Examples of commercially available products suitable for use in the present invention include, for example, Carbolag® 15 Plus from Lagos Industria Quimica.

Agents to Increase the Amount of Foaming

The oral care compositions of the invention also may include an agent to increase the amount of foam that is produced when the oral cavity is brushed.

Illustrative examples of agents that increase the amount of foam include, but are not limited to polyoxyethylene and certain polymers including, but not limited to, alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide.

The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Surfactants

Another agent optionally included in the oral care composition of the invention is a surfactant or a mixture of compatible surfactants. Suitable surfactants are those which are reasonably stable throughout a wide pH range, for example, anionic, cationic, nonionic or zwitterionic surfactants.

Suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference.

In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. Mixtures of anionic surfactants may also be utilized.

In another embodiment, cationic surfactants useful in the present invention can be broadly defined as derivatives of aliphatic quaternary ammonium compounds having one long alkyl chain containing about 8 to about 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof.

Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains about 8 to about 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

In a particular embodiment, the Composition of the Invention comprises an anionic surfactant, e.g., sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of about 0.1 to about 5% by weight and about 0.5 to about 1.5% by weight. The dosage of flavoring agent in the individual oral care composition dosage (i.e., a single dose) is about 0.001 to about 0.05% by weight and in another embodiment about 0.005 to about 0.015% by weight.

Chelating Agents

The oral care compositions of the invention also may optionally include one or more chelating agents able to complex calcium found in the cell walls of the bacteria. Binding of this calcium weakens the bacterial cell wall and augments bacterial lysis.

Another group of agents suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least about 1.0 wt. % pyrophosphate ions, about 1.5 wt. % to about 6 wt. %, about 3.5 wt. % to about 6 wt. % of such ions.

Polymers

The oral care compositions of the invention also optionally include one or more polymers, such as polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include about 1:4 to about 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139(M.W. 500,000), AN 119 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalkane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Enzymes

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. Nos. 4,992,420; 4,355,022; 4,154,815; 4,058,595; 3,991,177; and 3,696,191 all incorporated herein by reference. An enzyme of a mixture of several compatible enzymes in the current invention constitutes about 0.002% to about 2% in one embodiment or about 0.05% to about 1.5% in another embodiment or in yet another embodiment about 0.1% to about 0.5%.

Water

Water may also be present in the oral compositions of the invention. Water, employed in the preparation of commercial oral compositions should be deionized and free of organic impurities. Water commonly makes up the balance of the compositions and includes about 10% to about 90%, about 20% to about 60% or about 10% to about 30% by weight of the oral compositions. This amount of water includes the free water which is added plus that amount which is introduced with other materials such as with sorbitol or any components of the invention.

Humectants

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Suitable thickeners include naturally occurring polymers such as carrageenan, xanthan gum, polyglycols of varying molecular weights sold under the tradename Polyox, and polyvinylpyrrolidone. Compatible inorganic thickeners include amorphous silica compounds which function as thickening agents and include colloidal silicas compounds available under the trade designation Cab-o-sil manufactured by Cabot Corporation and distributed by Lenape Chemical, Bound Brook, N.J.; Zeodent 165 from J. M. Huber Chemicals Division, Havre de Grace, Md. 21078; and Sylodent 15, available from Davison Chemical Division of W. R. Grace Corporation, Baltimore, Md. 21203. Other inorganic thickeners include natural and synthetic clays such as hectorite clays, lithium magnesium silicate (laponite) and magnesium aluminum silicate (Veegum).

Methods of Manufacture

The compositions of the present invention can be made using methods which are common in the oral product area.

In one illustrative embodiment, the oral care composition is made by Method 2, described above, e.g., neutralizing arginine in a gel phase with an acid selected from: lactic acid, glycolic acid, citric acid, and acetic acid, succinic acid, or fumaric acid, and mixing to form Premix 1.

Actives such as, for example, vitamins, CPC, fluoride, abrasives, and any other desired active ingredients are added to Premix 1 and mixed to form Premix 2.

A toothpaste base, for example, dicalcium phosphate is added to Premix 2 and mixed. The final slurry is formed into an oral care product.

Composition Use

The present invention in its method aspect involves applying to the oral cavity a safe and effective amount of the compositions described herein.

The compositions and methods according to the invention are useful to a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit early enamel lesions, e.g., as detected by quantitative light-induced fluorescence (QLF) or electronic caries monitor (ECM).

Quantitative Light-induced Fluorescence is a visible light fluorescence that can detect early lesions and longitudinally monitor the progression or regression. Normal teeth fluoresce in visible light; demineralized teeth do not or do so only to a lesser degree. The area of demineralization can be quantified and its progress monitored. Blue laser light is used to make the teeth auto fluoresce. Areas that have lost mineral have lower fluorescence and appear darker in comparison to a sound tooth surface. Software is used to quantify the fluorescence from a white spot or the area/volume associated with the lesion. Generally, subjects with existing white spot lesions are recruited as panelists. The measurements are performed in vivo with real teeth. The lesion area/volume is measured at the beginning of the clinical. The reduction (improvement) in lesion area/volume is measured at the end of 6 months of product use. The data is often reported as a percent improvement versus baseline.

Electrical Caries Monitoring is a technique used to measure mineral content of the tooth based on electrical resistance. Electrical conductance measurement exploits the fact that the fluid-filled tubules exposed upon demineralization and erosion of the enamel conduct electricity. As a tooth loses mineral, it becomes less resistive to electrical current due to increased porosity. An increase in the conductance of the patient's teeth therefore may indicate demineralization. Generally, studies are conducted of root surfaces with an existing lesion. The measurements are performed in vivo with real teeth. Changes in electrical resistance before and after 6 month treatments are made. In addition, a classical caries score for root surfaces is made using a tactile probe. The hardness is classified on a three point scale: hard, leathery, or soft. In this type of study, typically the results are reported as electrical resistance (higher number is better) for the ECM measurements and an improvement in hardness of the lesion based on the tactile probe score.

The Compositions of the Invention are thus useful in a method to reduce early enamel lesions (as measured by QLF or ECM) relative to a composition lacking effective amounts of fluorine and/or arginine.

The Compositions of the invention are additionally useful in methods to reduce harmful bacteria in the oral cavity, for example methods to reduce or inhibit gingivitis, reduce levels of acid producing bacteria, to increase relative levels of arginolytic bacteria, inhibit microbial biofilm formation in the oral cavity, raise and/or maintain plaque pH at levels of at least about pH 5.5 following sugar challenge, reduce plaque accumulation, treat dry mouth, and/or clean the teeth and oral cavity.

Finally, by increasing the pH in the mouth and discouraging pathogenic bacteria, the Compositions of the Invention are useful to promote healing of sores or cuts in the mouth.

The compositions and methods according to the invention can be incorporated into oral compositions for the care of the mouth and teeth such as toothpastes, transparent pastes, gels, mouth rinses, sprays and chewing gum.

Enhancing oral health also provides benefits in systemic health, as the oral tissues can be gateways for systemic infections. Good oral health is associated with systemic health, including cardiovascular health. The compositions and methods of the invention provide particular benefits because basic amino acids, especially arginine, are sources of nitrogen which supply NO synthesis pathways and thus enhance microcirculation in the oral tissues. Providing a less acidic oral environment is also helpful in reducing gastric distress and creates an environment less favorable to Heliobacter, which is associated with gastric ulcers. Arginine in particular is required for high expression of specific immune cell receptors, for example T-cell receptors, so that arginine can enhance an effective immune response. The compositions and methods of the invention are thus useful to enhance systemic health, including cardiovascular health.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1: Formulations

Optimized arginine toothpaste formulations are prepared using the following ingredients:

TABLE A

| Material | Weight % | | | | |
| --- | --- | --- | --- | --- | --- |
| | Comp. A | Comp. B | Comp. C | Composition D | Composition E |
| Demineralized Water | q.s. | q.s. | q.s. | q.s. | q.s. |
| Flavor and Sweetener | 1.10 | 1.10 | 1.10 | 1.10 | 1.10 |

TABLE A-continued

| Material | | | | | |
|---|---|---|---|---|---|
| Dicalcium Phosphate Dihydrate | 40.00 | 40.00 | 40.00 | 40.00 | 40.00 |
| Glycerin | 18.00 | 18.00 | 18.00 | 18.00 | 18.00 |
| Polysaccharide | 1.32 | 1.32 | 1.32 | 1.32 | 1.32 |
| Anionic Surfactant | 1.43 | 1.43 | 1.43 | 1.43 | 1.43 |
| Sodium monofluoro phosphate | 1.10 | 1.10 | 1.10 | 1.10 | 1.10 |
| Tetrasodium pyrophosphate | 0.25 | 0.25 | 0.25 | 0.25 | 0.25 |
| Silica Thickening Agent | 1.00 | 1.00 | 1.00 | 1.00 | 1.00 |
| L-Arginine | 1.50 | 1.50 | 1.50 | 1.50 | 1.50 |
| Citric Acid | 0.5-1.1 (e.g., .0.60, 0.80, or 1.0) | | | | |
| Lactic Acid | | 0.5-1.1 (e.g., .0.60, 0.80, or 1.0) | | | |
| Glycolic Acid | | | 0.5-1.1 (e.g., .0.60, 0.80, or 1.0) | | |
| Acetic acid | | | | 0.5-1.1 (e.g., .0.60, 0.80, or 1.0) | |
| Hydrochloric Acid | | | | | 0.5-1.1 (e.g., .0.60, 0.80, or 1.0) |
| | 100.00 | 100.00 | 100.00 | 100.00 | 100.00 |

| Material | Composition 1 | Composition 2 |
|---|---|---|
| Demineralized Water | q.s. | q.s. |
| Flavor and Sweetener | 1.10 | 1.10 |
| Dicalcium Phosphate Dihydrate | 40.00 | 40.00 |
| Glycerin | 18.00 | 18.00 |
| Polysaccharide | 1.32 | 1.32 |
| Anionic Surfactant | 1.43 | 1.43 |
| Sodium monofluoro phosphate | 1.10 | 1.10 |
| Tetrasodium pyrophosphate | 0.25 | 0.25 |
| Silica Thickening Agent | 1.00 | 1.00 |
| L-Arginine | 1.50 | 1.50 |
| Citric Acid | | |
| Lactic Acid | | |
| Glycolic Acid | | |
| Succinic Acid | 0.5-1.1 (e.g., .0.60, 0.80, or 1.0) | |
| Fumaric Acid | | 0.5-1.1 (e.g., .0.60, 0.80, or 1.0) |
| | 100.00 | 100.00 |

TABLE B

| | Weight % | | | | |
|---|---|---|---|---|---|
| Material | Comp. F | Comp. G | Comp. H | Composition I | Composition J |
| Purified Water | q.s. | q.s. | q.s. | q.s. | q.s. |
| Flavor and Sweetener | 1.30 | 1.30 | 1.30 | 1.30 | 1.30 |
| Natural Calcium Carbonate | 42.00 | 42.00 | 42.00 | 42.00 | 42.00 |
| Sorbitol | 21.00 | 21.00 | 21.00 | 21.00 | 21.00 |
| Polysaccharide | 1.32 | 1.32 | 1.32 | 1.32 | 1.32 |
| Anionic Surfactant (e.g., 35% Sodium Lauryl Sulfate - Liquid) | 5.71 | 5.71 | 5.71 | 5.71 | 5.71 |

TABLE B-continued

| Material | | | | | |
|---|---|---|---|---|---|
| Sodium monofluorophosphate | 0.76 | 0.76 | 0.76 | 0.76 | 0.76 |
| Tetrasodium pyrophosphate | 0.25 | 0.25 | 0.25 | 0.25 | 0.25 |
| Synthetic Thickening Silica | 2.00 | 2.00 | 2.00 | 2.00 | 2.00 |
| Whitening agent | 0.75 | 0.75 | 0.75 | 0.75 | 0.75 |
| Sodium Carboxymethyl Celluose | 1.0 | 1.0 | 1.0 | 1.0 | 1.0 |
| Sodium Bicarbonate | 0.10 | 0.10 | 0.10 | 0.10 | 0.10 |
| Refined Soda Ash | 0.40 | 0.40 | 0.40 | 0.40 | 0.40 |
| Benzyl Alcohol | 0.30 | 0.30 | 0.30 | 0.30 | 0.30 |
| L-Arginine | 1.50 | 1.50 | 1.50 | 1.50 | 1.50 |
| Citric Acid | 0.25-1.0 (e.g., .0.35, 0.45, or 0.6) | | | | |
| Lactic Acid | | 0.25-1.0 (e.g., .0.35, 0.45, or 0.6) | | | |
| Glycolic Acid | | | 0.25-1.0 (e.g., .0.35, 0.45, or 0.6) | | |
| Acetic acid | | | | 0.25-1.0 (e.g., .0.35, 0.45, or 0.6) | |
| Hydrochloric Acid | | | | | 0.25-1.0 (e.g., .0.35, 0.45, or 0.6) |
| | 100.00 | 100.00 | 100.00 | 100.00 | 100.00 |

| Material | Composition 3 | Composition 4 |
|---|---|---|
| Purified Water | q.s. | q.s. |
| Flavor and Sweetener | 1.30 | 1.30 |
| Natural Calcium Carbonate | 42.00 | 42.00 |
| Sorbitol | 21.00 | 21.00 |
| Polysaccharide | 1.32 | 1.32 |
| Anionic Surfactant (e.g., 35% Sodium Lauryl Sulfate - Liquid) | 5.71 | 5.71 |
| Sodium monofluorophosphate | 0.76 | 0.76 |
| Tetrasodium pyrophosphate | 0.25 | 0.25 |
| Synthetic Thickening Silica | 2.00 | 2.00 |
| Whitening agent | 0.75 | 0.75 |
| Sodium Carboxymethyl Celluose | 1.0 | 1.0 |
| Sodium Bicarbonate | 0.10 | 0.10 |
| Refined Soda Ash | 0.40 | 0.40 |
| Benzyl Alcohol | 0.30 | 0.30 |
| L-Arginine | 1.50 | 1.50 |
| Citric Acid | | |
| Lactic Acid | | |
| Glycolic Acid | | |
| Succinic Acid | 0.25-1.0 (e.g., .0.35, 0.45, or 0.6) | |
| Fumaric Acid | | 0.25-1.0 (e.g., .0.35, 0.45, or 0.6) |
| | 100.00 | 100.00 |

Example 2

The production of acids by acidogenic oral bacteria leads to the demineralization of tooth enamel and overtime the development of dental caries. Catabolism of arginine via the arginine deiminase pathway by beneficial oral commensals results in base production (ammonia) which aids in the neutralization of plaque acids and the prevention of tooth decay. The ability of Streptococcus gordonii, a known arginolytic bacterium, to metabolize arginine present in the different formulas was evaluated in vitro. A colorimetric ammonia assay is used to quantify the resulting ammonia by spectrophotometry at 670 nm.

As shown in Table C below, in a planktonic ammonia assay to determine ammonia production, dentifrice formulations containing arginine resulted in the production of significantly higher ammonia versus the negative control—solutions containing 0.6% phosphoric acid, no arginine. Surprisingly, the choice of acid used in the formulation appears to play a role in the ability of S. gordonii to catabolize arginine. While the replacement of phosphoric acid with 1.2% sodium acid pyrophosphate, 0.7% hydrochloric acid, or 0.5% citric acid does not appear to have a significant effect on arginine degradation, and surprisingly perform approximately at parity (or possibly better) with positive control—(0.6% Phosphoric acid and 1.5% arginine). However, without being bound by theory, the remaining formulations possibly hinder ammonia production—compared to the positive control—as evidenced by the trend toward lower ammonia production in Table C.

TABLE C

| Dentifrice Samples* (by wt.) | Ammonia Production (nM) | Grouping** |
|---|---|---|
| 1.2% Sodium Acid Pyrophosphate | 0.98 | A |
| 0.6% Phosphoric Acid (Positive Control) | 0.91 | A, B |
| 0.7% Hydrochloric Acid | 0.89 | A, B |
| 0.5% Citric Acid | 0.87 | A, B |
| 0.7% Lactic Acid | 0.86 | B |
| 0.4% Succinic Acid | 0.82 | B |
| 0.6% Acetic Acid | 0.71 | C |
| 0.7% Fumaric Acid | 0.68 | C |

TABLE C-continued

| Dentifrice Samples* (by wt.) | Ammonia Production (nM) | Grouping** |
|---|---|---|
| 0.6% Phosphoric Acid, no arginine (Negative Control) | 0.08 | D |

*Unless indicated otherwise, all dentifrice samples contain comparable amounts of arginine.
**Samples which do not share a letter are significantly different.

Example 3

The Tables below indicate ageing studies performed using various test dentifrices. Unless otherwise indicated, the dentifrice samples all contain comparable amounts of dicalcium phosphate dihydrate and arginine, relative to each sample. Samples with "phosphoric acid" represent the positive control. As generally demonstrated in the stability assays below, Tables D-G, acids which are alternatives to the positive control, do not appear to negatively affect stability of fluoride or arginine over time in accelerated aging studies—i.e., relative to the positive control. This is surprising, and beneficial, given that there may be a preference to use acids other than phosphoric acid, given that they may be viewed as more "natural" alternatives. The temperatures in parentheses represent the conditions which the samples were exposed to during the aging study.

TABLE D

| | Dentifrice Samples | | | |
|---|---|---|---|---|
| | *F (ppm) | | | |
| % Acid (by wt.) | Initial | 1 month (40 C./75% RH) | 2 month (40 C./75% RH) | 3 month (30 C./65%/40 C./75%) |
| Phosphoric Acid 0.6% | 1500 | 1330 | 1260 | 1360/1150 |
| Succinic Acid 0.4% | 1830 | 1780 | — | — |
| Citric Acid 0.5% | 1450 | 730 | 970 | 1190/810 |
| Citric Acid 0.7% | 1470 | 760 | 1100 | 1260/930 |
| Acetic Acid 0.6% | 1490 | 650 | 1090 | 1210/930 |
| Hydrochloric Acid 0.7% | 1410 | 40 | 720 | 1000/570 |
| Lactic Acid 0.7% | 1430 | 590 | 840 | 1070/680 |
| Fumaric Acid 0.7% | 1460 | 970 | 1050 | |
| Sodium Acid Pyrophosphate 1.2% | 1480 | 1230 | 1040 | 1250/890 |

*sodium monofluorophosphate is fluoride source

TABLE E

| | Dentifrice Samples | | | |
|---|---|---|---|---|
| | Soluble Fluoride(ppm) (Range: Initial: 1305-1595/Aged: >=450) | | | |
| % Acid (by wt.) | Initial | 1 month (40 C./75% RH) | 2 month (40 C./75% RH) | 3 month (30 C./65% 40 C./75%) |
| Phosphoric Acid 0.6% | 1530 | 1380 | 1350 | 1450/1290 |
| Succinic Acid 0.4% | 1860 | 1890 | — | — |
| Citric Acid 0.5% | 1480 | 790 | 1120 | 1330/1020 |
| Citric Acid 0.7% | 1500 | 820 | 1250 | 1400/1150 |
| Acetic Acid 0.6% | 1520 | 680 | 1200 | 1330/1110 |
| Hydrochloric Acid 0.7% | 1460 | 440 | 920 | 1190/850 |
| Lactic Acid 0.7% | 1470 | 630 | 990 | 1230/900 |
| Fumaric Acid 0.7% | 1500 | 1040 | 1190 | — |
| Sodium Acid Pyrophosphate 1.2% | 1490 | 1360 | 1210 | 1370/1100 |

(TABLE E, continued)

TABLE F

Dentifrice Samples

| | Ionic Fluoride (ppm) | | | |
|---|---|---|---|---|
| % Acid (by wt.) | Initial | 1 month (40 C./75% RH) | 2 month (40 C./75% RH) | 3 month (30 C./65%-40 C./75%) |
| Phosphoric Acid 0.6% | 30 | 50 | 90 | 90/140 |
| Succinic Acid 0.4% | 30 | 110 | — | — |
| Citric Acid 0.5% | 30 | 60 | 150 | 140/210 |
| Citric Acid 0.7% | 30 | 60 | 150 | 140/220 |
| Acetic Acid 0.6% | 30 | 30 | 110 | 120/180 |
| Hydrochloric Acid 0.7% | 50 | 370 | 200 | 190/280 |
| Lactic Acid 0.7% | 40 | 40 | 150 | 160/220 |
| Fumaric Acid 0.7% | 40 | 70 | 140 | — |
| Sodium Acid Pyrosphosphate 1.2% | 10 | 130 | 170 | 120/210 |

(Table F, continued)

TABLE G

Dentifrice Samples

| | Arginine % (by wt.) | | | |
|---|---|---|---|---|
| % Acid (by wt.) | Initial | 1 month (40 C./75% RH) | 2 month (40 C./75% RH) | 3 month (30 C./65%-40 C./75%) |
| Phosphoric Acid 0.6% | 1.52 | 1.52 | 1.49 | 1.50/1.53 |
| Succinic Acid 0.4% | 1.53 | 1.47 | 1.49 | 1.47/1.48 |
| Citric Acid 0.5% | 1.51 | 1.5 | 1.48 | 1.49/1.49 |
| Citric Acid 0.7% | 1.51 | 1.52 | 1.48 | 1.48/1.50 |
| Acetic Acid 0.6% | 1.52 | 1.52 | 1.48 | 1.48/1.48 |
| Hydrochloric Acid 0.7% | 1.5 | 1.54 | 1.5 | 1.48/1.49 |
| Lactic Acid 0.7% | 1.5 | 1.53 | 1.47 | 1.49/1.49 |
| Fumaric Acid 0.7% | 1.49 | 1.51 | 1.47 | 1.49/1.47 |
| Sodium Acid Pyrosphosphate 1.2% | 1.51 | 1.45 | 1.52 | 1.46/1.47 |

Table G represents the value of arginine in the dentifrice samples in accelerated aging studies, wherein the amount of arginine is give in wt % of the total dentifrice sample.

The invention claimed is:

1. An oral care composition comprising
   i. an effective amount of arginine in free or salt form;
   ii. an effective amount of a soluble fluoride salt;
   iii. an abrasive, wherein the abrasive is dicalcium phosphate, present in an amount of 20%-60% by weight of the composition; and
   iv. an effective amount of a carboxylic acid; and
   wherein the carboxylic acid is selected from: citric acid, lactic acid, succinic acid, and any combination thereof, and wherein the carboxylic acid is present from 0.5 wt. %-1.1 wt. %, by weight of the composition.

2. The composition of claim 1, wherein the arginine comprises arginine in salt form, which is formed in situ in the formulation by neutralization of the arginine with an acid or a salt of an acid.

3. The composition of claim 1, wherein the amount of the carboxylic acid is effective to neutralize the arginine.

4. The composition according to claim 1, wherein the composition is an oral care composition in a form selected from: mouthrinse, toothpaste, tooth gel, tooth powder, non-abrasive gel, mousse, foam, mouth spray, lozenge, oral tablet, dental implement, and chewing gum.

5. The composition of claim 1, wherein the composition further comprises an inorganic acid, wherein the inorganic acid is not phosphoric acid or sulfuric acid, and wherein the inorganic acid is present from 0.5 wt. %-1.1 wt. %, by weight of the composition.

* * * * *